US00PP28549P3

(12) United States Plant Patent
Wells

(10) Patent No.: US PP28,549 P3
(45) Date of Patent: Oct. 24, 2017

(54) ***MAHONIA* PLANT NAMED 'MONRWS'**

(50) Latin Name: *Mahonia repens*
Varietal Denomination: MONRWS

(71) Applicant: Rick Wells, Dayton, OR (US)

(72) Inventor: Rick Wells, Dayton, OR (US)

(73) Assignee: Monrovia Nursery Company, Azusa, CA (US)

( * ) Notice: Subject to any disclaimer, the term of this patent is extended or adjusted under 35 U.S.C. 154(b) by 3 days.

(21) Appl. No.: 14/757,213

(22) Filed: Dec. 4, 2015

(65) Prior Publication Data

US 2017/0164537 P1 Jun. 8, 2017

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Mahonia* cultivar named 'MONRWS' is disclosed, characterized by greyed-purple fall foliage, yellow green Spring foliage and purple berries. The new variety is a *Mahonia*, typically produced as an outdoor ornamental plant.

3 Drawing Sheets

Latin name of the genus and species: *Mahonia repens.*
Variety denomination: 'MONRWS'.

BACKGROUND OF THE INVENTION

The new cultivar is the product of chance discovery. This new variety, hereinafter referred to as 'MonRws', was discovered as a naturally occurring, whole plant mutation by the inventor, Rick Wells. The interesting new mutation was discovered in a landscape planting in Dayton, Oreg. among a small population of unpatented, unnamed plants of *Mahonia repens* during Fall of 2010.

After identifying the new variety as a potentially interesting selection, the inventor first organized propagation of 'MONRWS' by air layers at a commercial nursery during July of 2011. The inventor continued controlled testing and propagation, assessing stability of the unique characteristics of this variety. At least five generations have been reproduced and have shown that the unique features of this cultivar are stable and reproduced true to type.

SUMMARY OF THE INVENTION

The cultivar 'MONRWS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MONRWS'. These characteristics in combination distinguish 'MONRWS' as a new and distinct *Mahonia* cultivar:

1. Distinctive greyed-purple fall coloration
2. Distinctive Yellow-Green foliage during Spring and Summer.
3. Purple berries.

PARENT COMPARISON

Plants of the new cultivar 'MONRWS' are similar to the parent, an unnamed *Mahonia repens* plant in most horticultural characteristics. The new variety, however, produces greyed-purple Fall foliage, compared to the year round green foliage of the parent. Additionally, berries of the new variety are purple, whereas berries of the parent variety are Violet-Blue.

COMMERCIAL COMPARISON

Plants of the new cultivar 'MONRWS' can be compared to the commercial variety *Mahonica repens* 'Cabaret' U.S. Plant Pat. No. 21,572. Plants of these cultivars are similar in most horticultural characteristics, however, 'MONRWS' differs in the following:

1. Greyed-Purple Fall foliage not found in this comparator variety.
2. The new variety has brighter yellow flowers.
3. The new variety is faster growing than the comparator.

Plants of the new cultivar 'MONRWS' can be compared to the unpatented unnamed *Mahonia nervosa* plant. Plants of these cultivars are similar in most horticultural characteristics, however, 'MONRWS' differs in the following:

1. Greyed-Purple Fall foliage not found in this comparator variety.
2. The new variety has solid yellow flowers, the comparator produces yellow flowers with orange streaks.
3. The new variety produces yellow-Green foliage, this comparator produces green foliage with a heavy bronze blush.

BRIEF DESCRIPTION OF THE PHOTOGRAPHS

The accompanying photograph in FIG. 1 illustrates in full color a typical plant of 'MONRWS' grown in Dayton, Oreg. Plant is approximately 3 years old, photographed in early Fall, as foliage begins turning purple.

Figure 1:
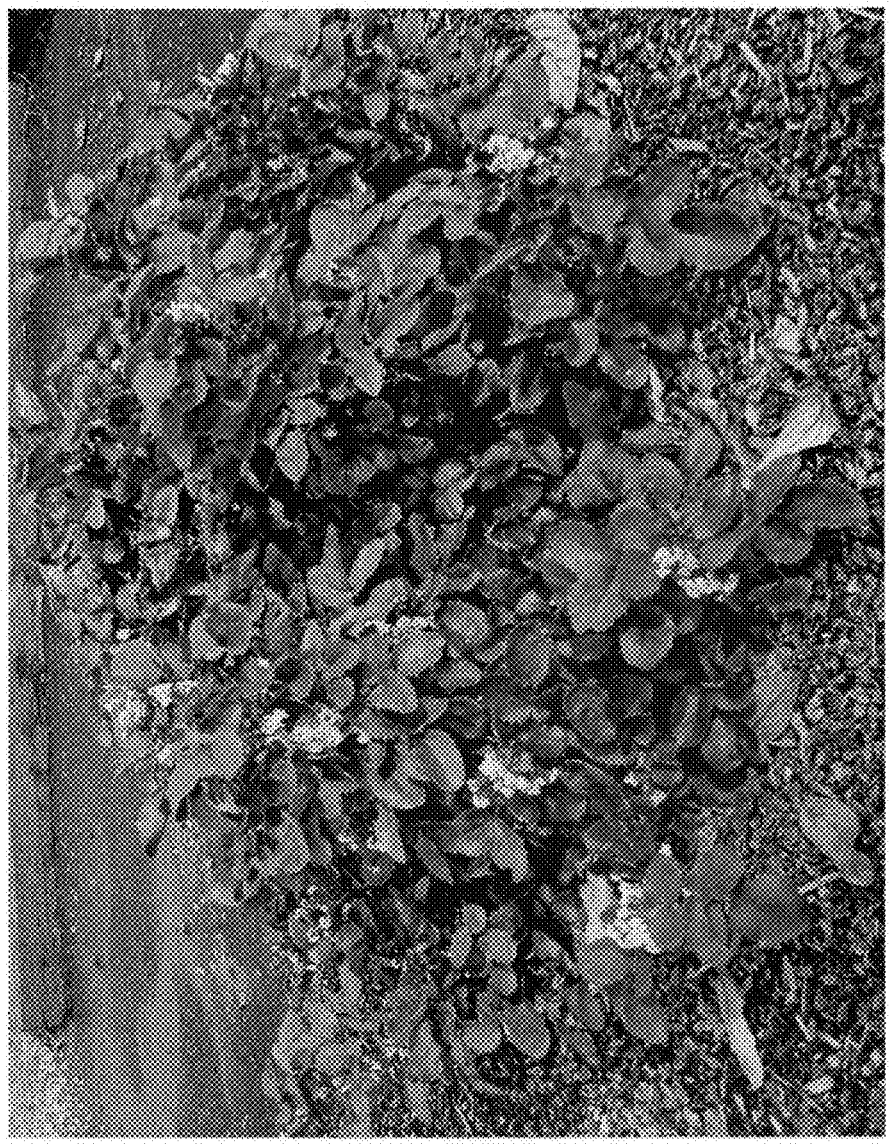
Figure 2:
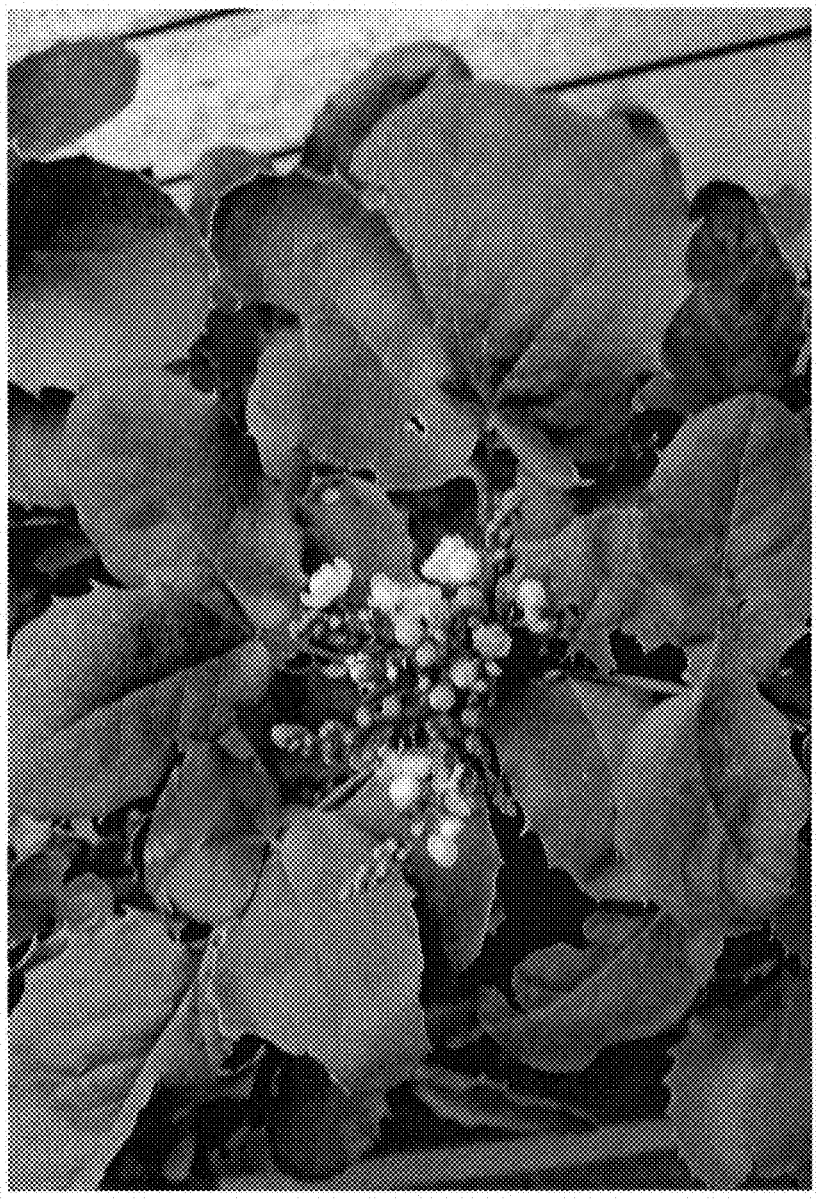
FIG. 2 illustrates in full color a close up of the late Fall foliage of 'MONRWS', having turned deepest greyed-purple.
Figure 3:
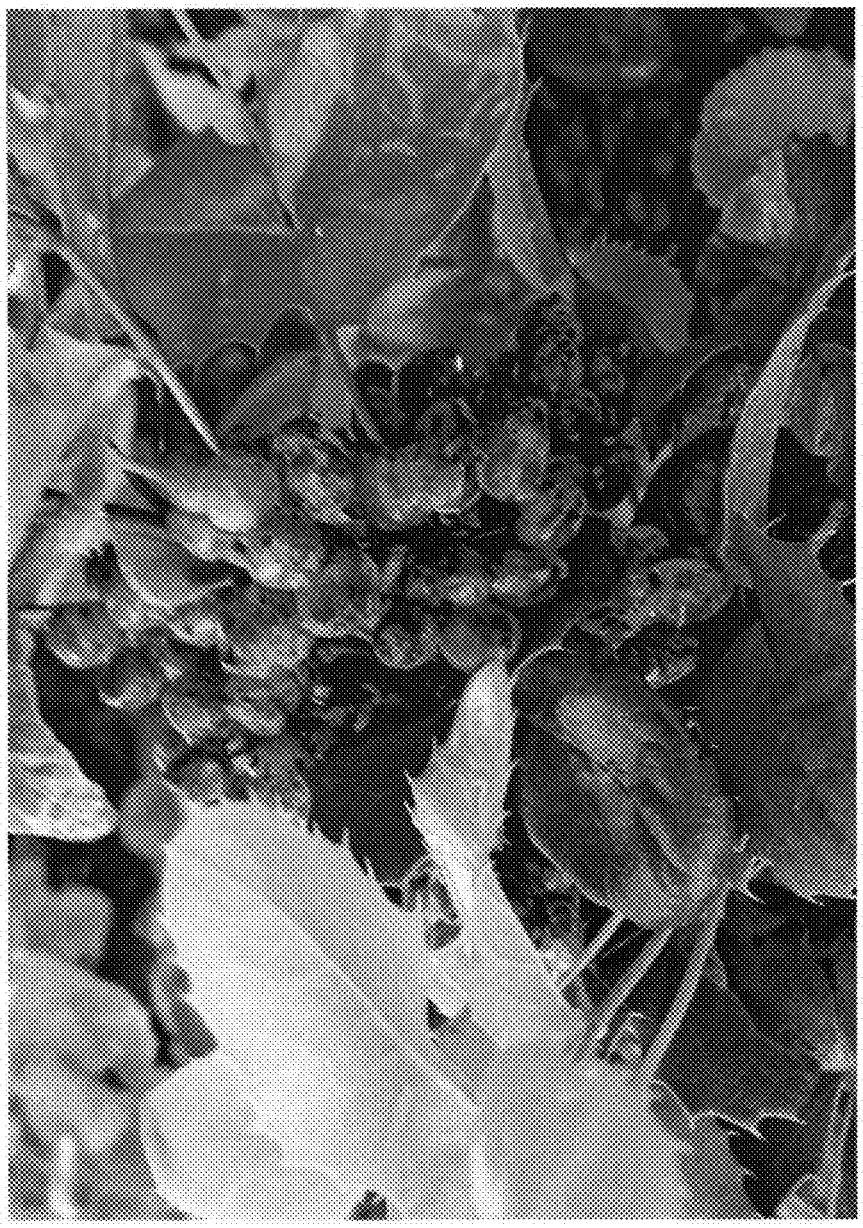
FIG. 3 illustrates a close up of berries.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'MONRWS' plants grown outdoors in Dayton, Oreg. Plants are approximately 1 years old. Temperatures ranged from approximately −1° C. to 15° C. at night and 10° C. to 32° C. during the day. No artificial light, photoperiodic treatments were given to the plants. No chemical treatments were given to plants. Measurements and numerical values represent averages of typical plant types.

Botanical classification: *Mahonia repens* 'MONRWS'.

PROPAGATION

*Mahonia repens* 'MONRWS' has been reproduced through tissue propagation.

PLANT

Growth habit: Roughly ovate, dense woody shrub.
Height: Approximately 90 cm for a two year old plant in a 5 gallon pot.
Plant spread: Approximately 90 cm.
Growth rate: Moderate to rapid.
Diameter of stem: Approximately 2.0 cm.
Length of stem: Average length ranges between 40 to 75 cm.
Color of stem: Mature stems near RHS Grey-Brown 197A to Grey-Brown N199A.
Texture of stem: Scaly and irregularly ridged.
Angle of stem: Lateral stems are straight and attached at acute angles between 60° to 90° degrees from the main stems.
Internode length: Between 5.0 and 15.0 cm; there are larger internode spaces closer to the base of the plant and smaller internode spaces near the apex of the plant.

FOLIAGE

Leaf:
- *Arrangement*.—Compound, composed of 5 leaflets.
- *Quantity*.—Approximately 8 leaves per lateral branch.
- *Average leaf length*.—Approximately 15.0 cm.
- *Average leaf width*.—Approximately 7.0 cm.
- *Rachis*.—Length: Average 8.0 cm. Diameter: 4 mm. Texture: Glabrous to very slightly scabrous. Color: Emerging foliage near Yellow-Green 150B, mature foliage Yellow-Green N144A covered in a flush of Greyed-Red 181B. Fall Foliage near Greyed-Purple 183C.

Leaflets:
- *Shape of blade*.—Deltoid.
- *Apex*.—Broadly acuminate.
- *Base*.—Truncate.
- *Margin*.—Sharply serrate.
- *Attachment*.—Sessile.
- *Texture of top surface*.—Glabrous.
- *Texture of bottom surface*.—Glabrous.
- *Appearance upper surface*.—Matte.
- *Appearance lower surface*.—Matte.
- *Aspect*.—Undulating.
- *Color*.—Young foliage upper side: Near RHS Yellow-Green N144B. Young foliage under side: Near RHS Yellow-Green N144A. Mature foliage upper side: Near RHS Green 137A. Mature foliage under side: Near RHS Yellow-Green 147B. Edges of mature plant fade to: Near RHS Red-Purple 59B.
- *Venation*.—Type: Pinnate. Venation color upper side: Near RHS Green 137D. Venation color under side: Near RHS Green 138B.
- *Petiole*.—Length: Average 4.5 cm. Diameter: Approximately 0.15 cm. Color: Near RHS Yellow-Green 144A. Texture: Glabrous.
- *Fall color*.—Upper side: Near RHS Greyed-Purple 185B, turning to Greyed-Purple N187A. Under side: Near RHS Red 53A turning to Greyed-Purple 187D.

FLOWER

Natural flowering season: Summer.
Inflorescence and flower type and habit: Fascicled raceme composed of perfect, upwardly cupped flowers.
Flowers per inflorescence: Average range 30 to 60.
Inflorescence size:
- *Diameter*.—Average range from about 7 cm to 13 cm.
- *Height*.—Average range from about 9 cm to 17 cm.

Flower longevity on plant: 7 to 10 days, self-cleaning.
Bud:
- *Shape*.—Globular.
- *Length*.—4 mm.
- *Diameter*.—5 mm.
- *Color*.—Near RHS Green 141C.

Flower size:
- *Diameter*.—9 mm.
- *Height*.—5 mm.

Petals:
- *Length*.—3 mm.
- *Diameter*.—2 cm.
- *Quantity*.—6 or 8.
- *Texture*.—Glabrous.
- *Apex*.—Acute.
- *Base*.—Truncate.
- *Margin*.—Entire.
- *Color*.—When opening: Upper surface: Near RHS Yellow-Green 1A. Lower surface: Near RHS Yellow-Green 1A. Fully opened: Upper surface: Near RHS Yellow 5A. Lower surface: Near RHS Yellow 5A.

Corolla: Cup-shaped, approximately 9 mm in diameter, 5 mm in height.
Sepals:
- *Quantity per flower*.—6.
- *Shape*.—Ovate.
- *Length*.—4 mm.
- *Width*.—3 mm.
- *Apex*.—Acute.
- *Base*.—Truncate.
- *Margin*.—Entire.
- *Texture*.—Glabrous.

*Color*.—Near RHS Green 141C, upper and lower surfaces.

Peduncle:

*Length*.—Average range 5 to 12 cm.

*Diameter*.—4 mm.

*Color*.—Near RHS Yellow-Green 147A flushed Greyed-Purple N187A.

*Strength*.—Moderately strong.

*Angle*.—30° to 90° angle from stem.

Pedicel:

*Length*.—About 5 mm.

*Diameter*.—About 3 mm.

*Color*.—Near RHS Green 141C.

Fragrance: Faint sweet scent.

REPRODUCTIVE ORGANS

Stamens:

*Number*.—6.

*Filament length*.—15 mm.

*Filament color*.—Near RHS Yellow-Green 150D.

Anthers:

*Shape*.—Oblong.

*Length*.—3 mm.

*Color*.—Near RHS Yellow 6A.

Pollen:

*Color*.—Near RHS Yellow 6A.

*Quantity*.—Scant.

Pistil:

*Quantity*.—1.

*Length*.—3 mm.

*Style*.—Reduced, indistinguishable.

*Ovary*.—Diameter: 1 mm. Color: Near RHS Yellow-Green 144C.

OTHER CHARACTERISTICS

Fruits: Berry. Globose, approximately 9 mm diameter. Glossy, smooth. Colored near Purple N79A.

Seed: 1 to 5 per fruit. Flattened sphere, 4 mm long, 3mm diameter. Colored near Greyed-Orange 164D.

Disease/pest resistance: Neither resistance nor susceptibility to the normal diseases and pests of *Mahonia* has been observed.

Temperature tolerance: USDA Zones 5-9.

Drought tolerance: Will tolerate some dryness once established.

What is claimed is:

1. A new and distinct cultivar of *Mahonia* plant named 'MONRWS' as herein illustrated and described.

* * * * *